US007913538B2

(12) United States Patent
Brassier et al.

(10) Patent No.: US 7,913,538 B2
(45) Date of Patent: Mar. 29, 2011

(54) EVALUATION METHOD FOR MONITORING THE EFFECTS OF AN IMPACT ON A STRUCTURAL COMPOSITE MATERIAL PART

(75) Inventors: Pascale Brassier, Martignas sur Jalles (FR); Patrick Peres, Saint Aubin de Medoc (FR)

(73) Assignee: Eads Space Transportation SAS, Paris (FR)

( * ) Notice: Subject to any disclaimer, the term of this patent is extended or adjusted under 35 U.S.C. 154(b) by 1084 days.

(21) Appl. No.: 10/578,582

(22) PCT Filed: Sep. 17, 2004

(86) PCT No.: PCT/FR2004/050442
§ 371 (c)(1), (2), (4) Date: Aug. 10, 2006

(87) PCT Pub. No.: WO2005/045389
PCT Pub. Date: May 19, 2005

(65) Prior Publication Data
US 2007/0050153 A1      Mar. 1, 2007

(30) Foreign Application Priority Data

Nov. 5, 2003    (FR) .................................... 03 12992

(51) Int. Cl.
*G01N 3/30*    (2006.01)
(52) U.S. Cl. ................................................... 73/12.01

(58) Field of Classification Search ................. 73/12.01, 73/762
See application file for complete search history.

(56) References Cited

U.S. PATENT DOCUMENTS

| 4,104,910 | A | * | 8/1978 | Ogata et al. | ................ 73/862.53 |
| 5,059,261 | A | * | 10/1991 | Condo et al. | ................ 149/19.92 |
| 6,033,987 | A | * | 3/2000 | Lin et al. | ........................ 438/692 |
| 6,564,641 | B1 | * | 5/2003 | Shigyo | ........................... 73/705 |
| 6,668,661 | B2 | * | 12/2003 | Rider | .............................. 73/762 |
| 7,647,809 | B1 | * | 1/2010 | Cooney | ........................ 73/12.01 |
| 2002/0000128 | A1 | * | 1/2002 | Williams | ........................ 73/762 |
| 2002/0129658 | A1 | | 9/2002 | Rider | |

FOREIGN PATENT DOCUMENTS

| EP | 0 538 580 A | 4/1993 |
| GB | 2 107 213 A | 4/1983 |
| GB | 2 194 062 A | 2/1988 |

OTHER PUBLICATIONS

K. Hoffmann et al., "Computer Aided Evaluation of Pressure Measurements on Crane Runways by Means of Fuji Prescale Film," VDI Berichte Nr. 69:367-379 (1988).

* cited by examiner

*Primary Examiner* — Freddie Kirkland, III
(74) *Attorney, Agent, or Firm* — Patterson Thuente Christensen Pedersen, P.A.

(57) ABSTRACT

An evaluation method for monitoring the consequences of an impact at low speed and little force on a structural composite material part covered with a film that changes color when under pressure and whose color intensity is directly related to the force of a received shock.

4 Claims, 1 Drawing Sheet

12 Joules 6,8 Joules

1 Joule

EVALUATION METHOD FOR MONITORING THE EFFECTS OF AN IMPACT ON A STRUCTURAL COMPOSITE MATERIAL PART

RELATED APPLICATIONS

This application is a national stage entry of PCT Application No. PCT/FR2004/050442 filed Sep. 17, 2004, and French Application No. 0312992 filed Nov. 5, 2003.

FIELD OF THE INVENTION

The present invention pertains to detecting impacts on structural parts made from composite material.

BACKGROUND OF THE INVENTION

Composite materials, which are made up of mineral, organic, synthetic, or natural fibers or filaments held together in an organic polymer matrix, have excellent static and dynamic mechanical properties (resistance to fatigue) in a low density.

Structural parts generally requiring both optimal mechanical properties and low mass are those with the best possible bond of these materials, and built with precision.

Composite materials are generally fragile. They can be sensitive particularly to shocks (or impacts), which can produce delamination and material integrity loss due to the fact that they contain layering of different materials and can have poor elasticity, with breakage occurring 1% of the time.

Their use in industrial environments therefore requires special precautions, or over-sizing which can cause them to lose part of their bonding.

SUMMARY OF THE INVENTION

An object of this invention is to enable a lasting means by which to passively monitor the composite materials throughout their entire life, from their manufacture to their retirement from use, so as to assure continuous integrity and functionality.

More precisely, this invention concerns the detection of impacts that result from "low force" shocks. These are the small shocks of everyday life, as those generated by a falling instrument: their speed being measured in m/s and their force being measured at approximately ten joules.

At the time of the "low force" shocks, the mechanisms at work function like a classic mechanical application—the material undergoes a compression that transforms it into a triaxial stress state. Depending upon the level of this stress state, there may be a break or simple (reversible) material damage.

The stress from the shocks add to the stress already in the material, which can be dependent upon the geometry of the item concerned and the manner by which the stress comes about, so that a similar shock could not induce the same material deterioration. In any case, shocks would react differently according to the shape of the object generating the impact.

The detection of this type of shock commonly occurs using the composite materials.

One may examine composite material parts in general, notably parts intended for use on airplanes, using a procedure called BVID (Barely Visible Impact Damage), on a fixed depth threshold of 0.3 mm for marks stemming from a detectable shock when the surface is otherwise uniform, beyond which the part is considered defective.

Of course, this approach can be limited in that one cannot consider all of the characteristics of composite materials, as a reduction must be made for the BVID, leading to the manufacture of parts with a safety measure.

The present invention is not concerned with this type of part, but more precisely on the mechanical/mass of structural composite material parts, that is, on the most precisely sized parts with a reduced safety margin.

This can be the case, for example, in the domain of thrusters for pressure tanks made from composite materials, used either to pressurize engines, to contain erbium or similar gas or liquid storage, or as a wrap for powder propellers.

These tanks generally contain an "internal skin," more commonly called a liner, on which a pre-engaged resin fiber can be wound.

The fibers are carbon, glass, or Kevlar, and the resin can be epoxide, polyester, or some other material.

The liner serves mainly to satiate the tank. It can have other functions as well, such as serving as a heat insulator for a powder propeller wrap.

Because they are used in space, these tanks are optimally developed, partially without margin. The burst pressure is only 1.5 times the service pressure, and any deterioration of the composite material can have catastrophic consequences. Therefore, it is understandably very important to be able to guarantee that these tanks are structurally perfect and particularly that they have not undergone any non-detectable shocks.

It is not currently possible to provide a guarantee that such tanks have not previously undergone any very strong impacts.

In fact, it is also impossible to detect "low impact" shocks using the current method.

Known methods for shock detection fall into two categories: (1) analysis of material by mass and (2) analysis of material on the surface.

The first of these is certainly interesting, but it uses complex techniques, such as sound emission or fiber optics, which are still under research, and they require a means for manipulating the complex and voluminous signal, a test that cannot easily be performed throughout the life of a given part.

The second method involves coatings that must be analyzed, notably by visual examination.

The principle behind these methods for visual examination are known to those skilled in the art. The principle is described, for example, in GB 2 194 062 and FR 2 663 122, which are both incorporated herein by reference in their entirety.

By this principle, microcapsules within a product break apart when subject to a certain level of pressure. These products are preferably fluorescents—like dye-penetrant—and testing these parts for evidence of shock generally can be done with an ultraviolet light.

The complicated nature of researching defects, owing to the fact that these products are solid and stable within a large range of temperature and of hygrometry before and after detection, explains why these methods are not used.

Another point to note is that the concept of detection accomplishes only qualitative shock detection and not any quantitative shock detection whatsoever.

In fact, such detection provides only an indication that pressure of a certain value has been applied to the surface of the examined material with no indication of the magnitude of possible structural problems caused within the underlying layers of the impacted zone.

This invention provides a method using visual examination for detection, enabling a relationship between what is observed and the quantitative method for shocks. That is, it correlates the force of the shocks and the damage evident on the impacted material.

To this effect, the invention includes an evaluation method for monitoring the consequences of an impact on a structural composite material part, notably the impact at low speed and little force. The part can be covered with a film that changes color when under pressure and whose color intensity can be directly related to the force of the received shock, as characterized in that, before the application of the film on the part:

the film is calibrated by testing the impact on test parts that are identical to the said part, or on test tubes representative of this, covered in said film, in order to establish a link between the force of the shock and the change in the film, the impacted areas of the test parts or test tubes are evaluated by means of an appropriate qualification method using x-ray, ultrasound, or another method, in order to correlate the aforementioned changes in the film as well as the nature and extent of the possible structural disturbance of subjacent layers of the impacted area, and a scale of correspondences is established, allowing for qualification against a limiting threshold for acceptance of the evaluated part.

A structural composite material part thus covered in said film can be monitored over the life of the part, from its manufacture to its use or its retirement from use, through a simple visual examination at any moment in time. If during such a test, the part reveals an impact that corresponds to a position on the aforementioned scale of correspondences at a level equal to or higher than the defined threshold, the part will be taken out of service due to internal damage rendering it unable to function.

Useable film pursuant to the invention can be comprised of a flexible complex with a matrix containing drowned microcapsules or similar that break up under stress, releasing their contents which have different optical properties depending on whether they are encapsulated or released within the matrix. The shells of the microcapsules can be sensitive to constraints of different intensities. The matrix can be mainly a resin, the final product being either a picture or a film to adhere to the said part.

A highly recommended product implementing the method in this invention is a film marketed under the commercial name PRESSUREX® by Sensor Products, Inc. of East Hannover, N.J. in the United States of America.

This film comprises a sandwich formed of two thin polyester films between which are a layer of microcapsules and an indicator layer for color. These microcapsules are susceptible to bursting under the effect of measured pressure, thereby coloring the subjacent indicator layer, whose intensity of color can be directly related to the amount of pressure (expressed in joules) that was applied to the film.

Other types of shock indicator film may be used, of course, provided that they adhere to the same principle, incorporating microspheres, microtubes, and similar, susceptible to bursting under pressure and consequently changing color.

DETAILED DESCRIPTION OF THE DRAWINGS

Figure 3:
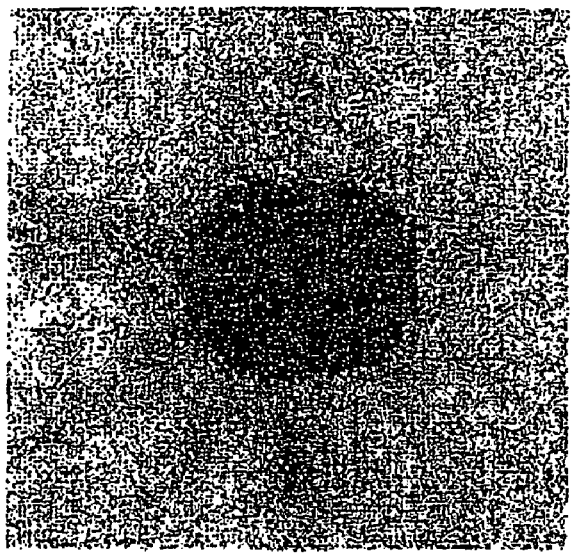
FIG. 3 depicts a mark resulting from a force of 12.0 joules.
Figure 1:
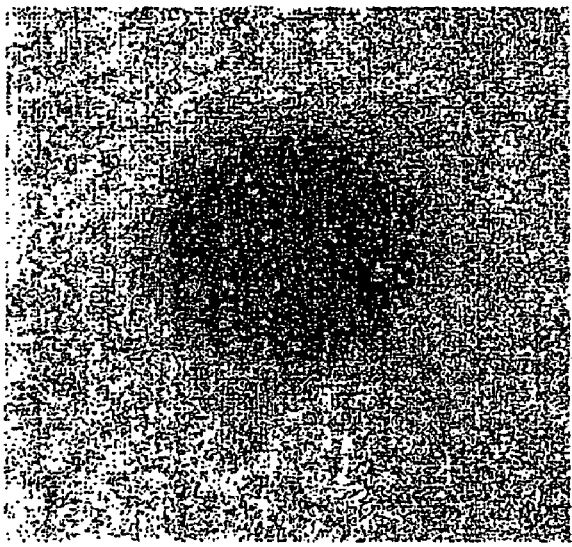
FIG. 1 depicts a "high"-impact mark resulting from a force of 6.8 joules.
Figure 2:
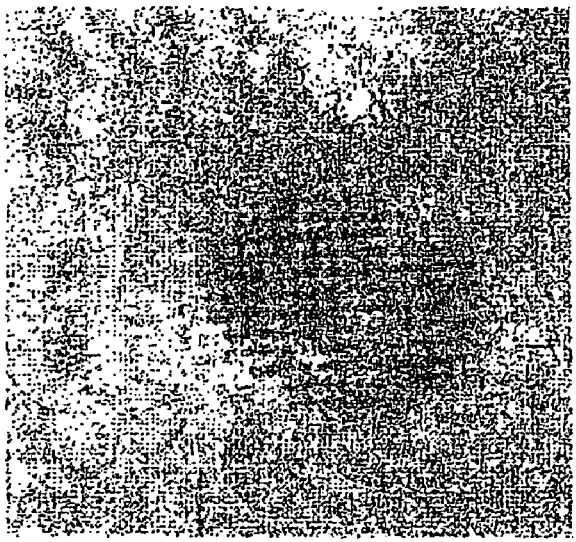
FIG. 2 depicts a mark resulting from a force of 1.0 joules.

Referring to FIGS. 1-3, pursuant to the invention, impact tests are used to calibrate film. To that effect, impact tests at various force levels are performed, ideally on sample parts that are identical to the subject part but more generally on test tubes representing the part, to establish a correspondence scale of these various force levels based upon the visual result of each test, namely a gradation of color intensity, since this can be the result of the amount of force applied at the time of the shock.

Through this process, a full range of impact prints will be developed, corresponding to a given range of impact force. The prints will be distinguishable from one another by one level of color intensity whose gradation can be noticeable by the density and extent of the colored elements of FIG. 1.

Then, for each test tube, the impacted area will be evaluated (that is, examined using the appropriate method, such as x-ray or ultrasound) in order to identify possible disturbances in layers subjacent to the mark, as revealed by a change in the distribution of constraints in the mass of the test tube and resulting in the reorientation of some layers, even interlaminary shearing, creating delamination of layers and making the composite material unfit for use.

FIG. 1 illustrates a "high"-impact mark produced on a PRESSUREX® film and resulting from a pressure of 500-1300 bars, placed on a test tube with 100 mm×150 mm surface area and 2 mm thickness, comprising a certain number of folds in the composite material wrapping. The said test tube has been impacted by a spherical-headed object, in accordance with the AITM standard 1.0010 Edition 2 of June 1994. The impact mark depicted in FIG. 1, which is 13 mm in diameter, is the result of a force of 6.8 joules.

FIG. 1 depicts an image of an impact of 6.8 joules, which proved to generate a disturbance to an intolerable extent. As a result, the mark in the figure can be treated as a threshold triggering the removal or taking out of service of any part fit with a film that can be identical to that in FIG. 1 and that, upon visual inspection, bears a mark of the same color intensity as that shown in FIG. 1.

Referring to FIG. 2, if the inspected part contains a mark like that in FIG. 2, which is less dense in color than the mark in FIG. 1, this will signal an impact with less force (1 joule) than that of the impact in FIG. 1, and it would not trigger the part as unusable.

Referring to FIG. 3, if, on the contrary, the visual test shows a mark like that in FIG. 3, with a density that is more intense in color than that in FIG. 1 (corresponding to an impact with a force of 12 joules), the part will be rejected or replaced, a fortiori.

PRESSUREX® films are available commercially as a line of products with various "sensitivities" to pressure. For example, "Low" film can be usable for 25-100 bars, "Medium" can be usable for 100-500 bars, and "High" can be usable for 500-1300 bars.

Film can be selected according to the kind of parts involved (that is, so that the force of impact not causing crippling damage would fall within the range of pressure "sensitivity" for the film).

Because calibration tests conducted on full-scale parts or on pieces of such parts generally prove to be expensive, it may be preferable to perform calibration tests on test tubes of a reduced size, representative of the part being tested, such as by modeling test-tubes to have the same rigidity of indentation as the area being studied on the actual part.

Note also that tests have shown that PRESSUREX® film can be particularly stable by temperature. In other words, the behavior of film in respect to the same force of impact is consistent across various temperatures.

That is, a sample of film remaining at 70° C. for about 45 minutes and a sample at room temperature both contained impact marks that were substantially identical for the same force of impact. Such stability is also observed over time. So, film that received a calibrated impact and then was exposed to a temperature of 130° C. for 1 hour did not change its colored mark, which is consistent with a recent impact.

The parts monitoring method in the invention is reliable and adaptable to complex conditions of use.

Through simple periodic visual monitoring of parts, this method allows one to instantaneously determine at any moment whether a part in question satisfies an integrity test or, by contrast, whether it has undergone impacts that may have caused damage, regardless of the amount of time that may have passed between the impacts and the time of monitoring or whether the temperature of the room varied (even substantially) before or after the aforementioned impacts.

The method in the invention applies to a wide range of structural composite parts and particularly to structural composite reservoirs for space use, such as gas or liquid tanks under high pressure, as used for space launches, spherical, cylindrospherical, cylindro-elliptical or toric in shape and consisting of an impermeable internal metal or plastic layer upon which are wound pre-engaged resin fibers.

The invention claimed is:

1. An evaluation method for monitoring consequences of an impact at low speed and force on a structural composite material part covered with a film that changes color when under pressure and whose color intensity is directly related to a received shock force, the method comprising:

calibrating a film by testing an impact on test parts covered in the film that are identical to a structural composite material part or on test tubes covered in the film, the test tubes being representative of the structural composite material part, to establish a link between a received shock force and a change in color in the film;

evaluating impacted areas of the test parts or test tubes using an appropriate qualification method selected from the group consisting of x-ray or ultrasound to correlate the change in color in the film and a nature and extent of any structural disturbance of subjacent layers of the impacted area; and establishing a scale of correspondences enabling qualification against a limiting threshold for acceptance of the structural composite material part covered with the film.

2. The method of claim 1, wherein the structural composite material part comprises a high-pressure gas or liquid tank usable for space launches, the structural composite material part comprising an impermeable internal metal or plastic layer upon which pre-engaged resin fibers are wound.

3. The method of claim 1, wherein the film comprises a matrix with drowned microcapsules susceptible to breaking up under stress of a determined threshold of force.

4. The method of claim 3, wherein the structural composite material part comprises a high-pressure gas or liquid tank usable for space launches, the structural composite material part comprising an impermeable internal metal or plastic layer upon which pre-engaged resin fibers are wound.

* * * * *